United States Patent [19]

Daneshvar

[11] Patent Number: 5,363,843
[45] Date of Patent: Nov. 15, 1994

[54] SPECIAL INSTRUMENT COVERS

[76] Inventor: Yousef Daneshvar, 21459 Woodfarm, Northville, Mich. 48167

[21] Appl. No.: 31,890

[22] Filed: Mar. 16, 1993

[51] Int. Cl.⁵ .............................. A61B 1/00; A61B 5/00
[52] U.S. Cl. ........................................ 128/630; 128/4; 128/7; 128/8; 128/9; 128/917
[58] Field of Search ............... 128/630, 917, 918, 919, 128/4, 6, 8, 7, 9

[56] References Cited

U.S. PATENT DOCUMENTS

| 4,646,722 | 3/1987 | Silverstein et al. | 128/4 |
| 4,809,678 | 3/1989 | Klein | 128/4 |
| 5,201,908 | 4/1993 | Jones | 128/4 |

Primary Examiner—William E. Kamm
Assistant Examiner—Brian M. Green

[57] ABSTRACT

In an area where deadly diseases such as AIDs and similar diseases are common, the need for cleanness is obvious. This application provides covers made from latex and methods of using them that will be used to cover endoscopes and their parts to prevent such contaminations.

26 Claims, 10 Drawing Sheets

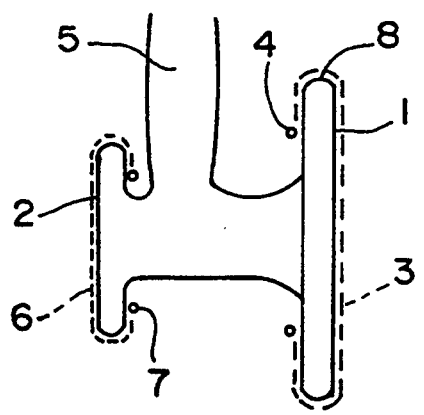
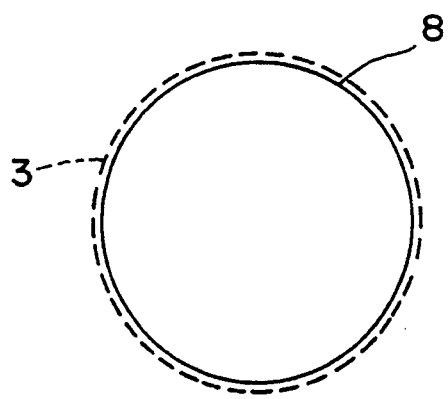
FIG. 1          FIG. 2
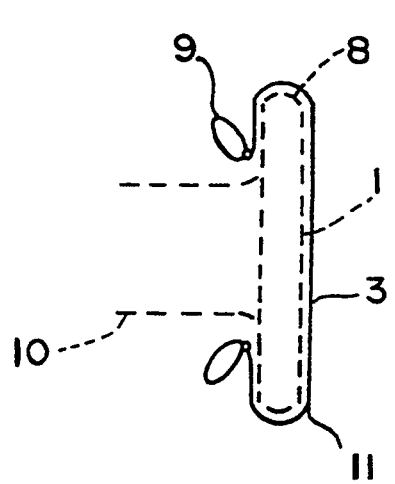
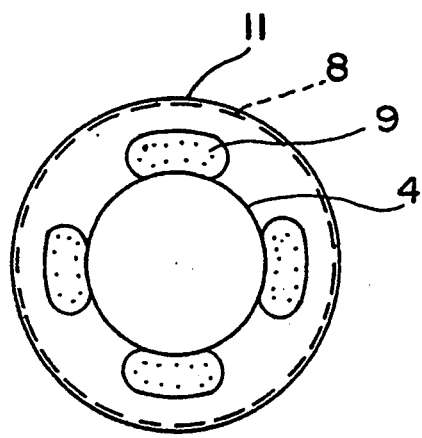
FIG. 3          FIG. 4

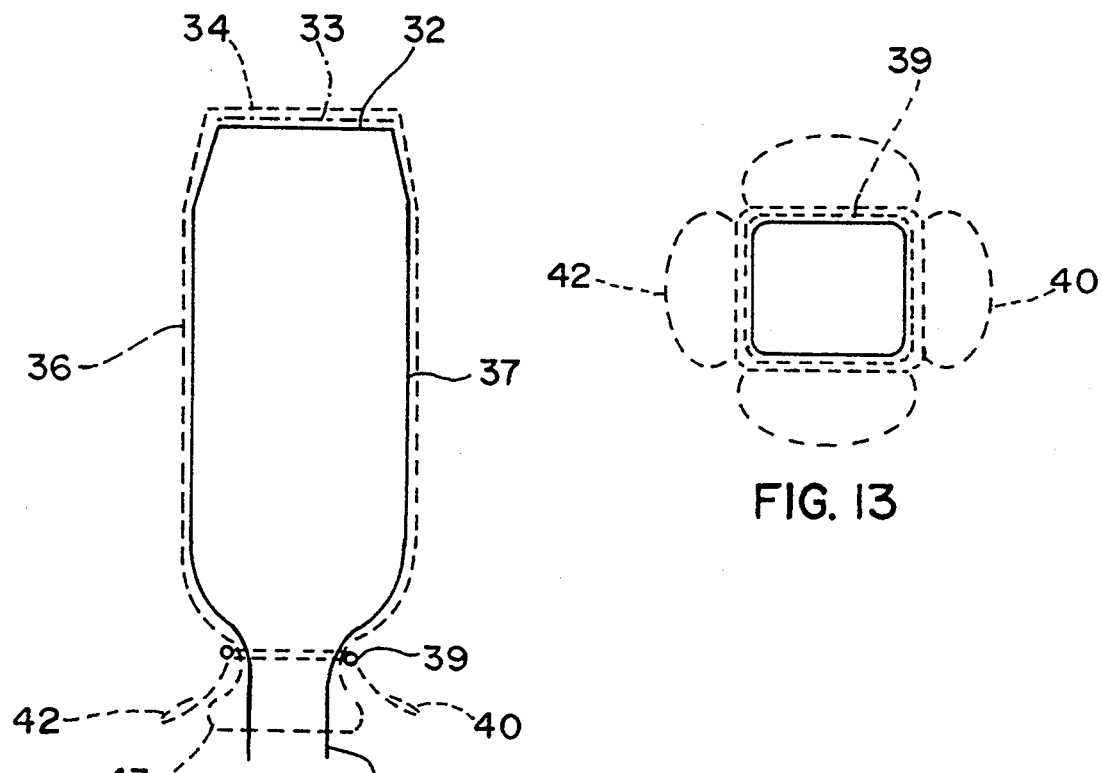
FIG. 13
FIG. 12
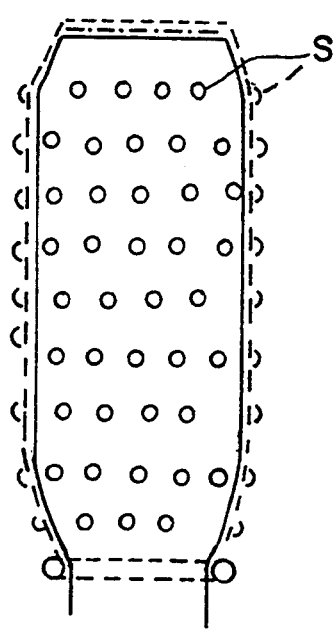
FIG. 14

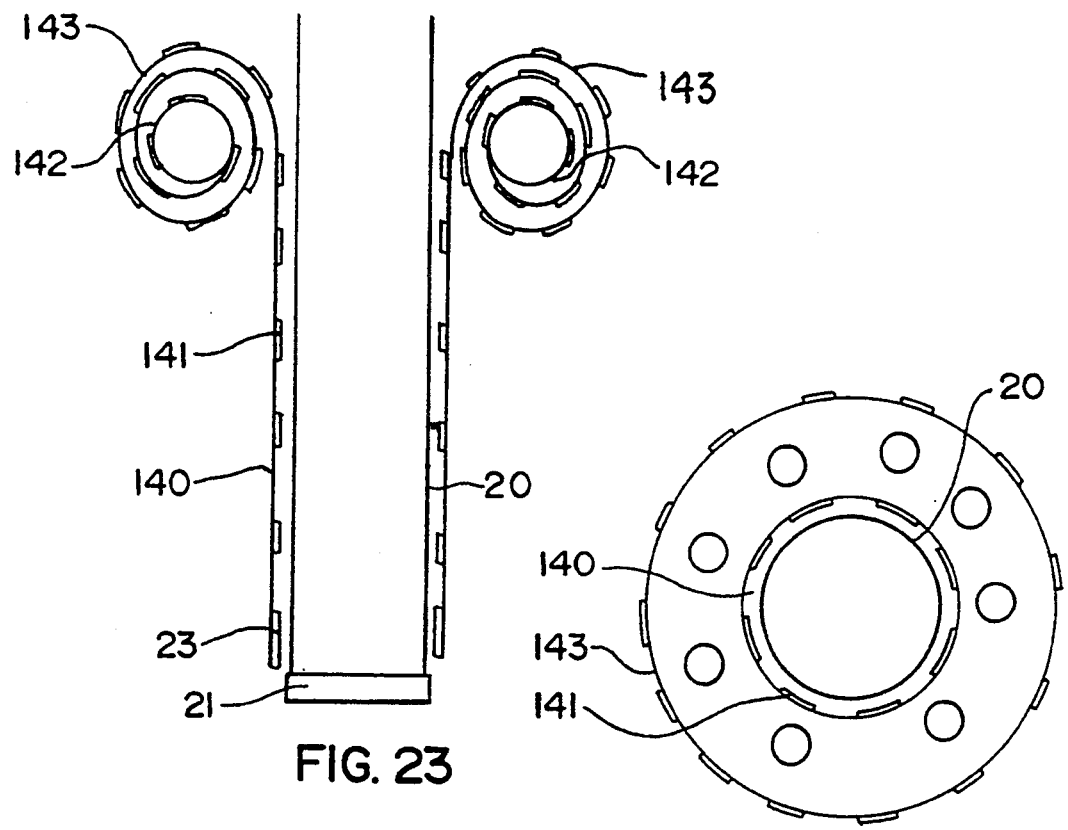
FIG. 23
FIG. 24
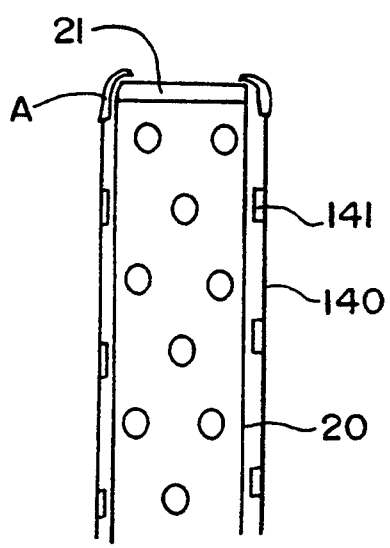
FIG. 25

SPECIAL INSTRUMENT COVERS

BACKGROUND OF THE INVENTION

The introduction of HIV to human life has made a tremendous impact in the way medicine is practiced. New concerns have been raised, and the need for perfect cleanness and sterilization has turned to be a very important demand. This deadly virus, which has claimed hundred thousands of lives, has set a fear among the people and doctors that is unbelievably deep-seated and extremely important.

One very important issue exists. Since the period between contamination and the full-blown picture of the disease is a very long one, this prevents us from finding an easy cause and effect relation; therefore at times it gets very difficult, or in fact impossible, to find which caused which. Also this disease has taught everyone that small germs are truly important and should not be ignored by any means. This also brought the possibility that maybe there are other disease and problems that are caused by small yet unknown germs. Even a question has come up that maybe some sort of cancers are indeed caused by viruses that we simply have not identified. This background mandates the best possible prevention techniques be used.

However, the technique of cleaning some medical instruments, such as endoscopes, is in my mind not perfect. In practice these units are used bare in patients and are subject to being contaminated by millions of many small ultramicroscopic materials, such as AIDs virus. They are cleaned manually and that is subject to human error. Please notice that these germs cannot be seen even by microscopes. The diagnosis of such occurrence will be very difficult since as mentioned earlier the period between the contamination and actual disease is a very long one and does not allow this to be recognized. These give grounds to some people to worry that the endoscopes or transducers used on them could be contaminated and start a nidus for a deep seated worry that cannot be relieved since there is no easy way for early diagnosis of diseases such as AIDs.

So the answer to this problem is to prevent such contamination as best as possible. However in practice the means for such prevention from contaminations of endoscopes does not exist, or at least the inventor of this unit is not aware of them. Therefore this unit is introduced for such important purpose.

SUMMARY OF THE INVENTION

This technique uses a latex or plastic cover which is commonly used in the medical field for prevention of contamination from germs. This material, which is used in making surgical gloves, will be very useful in prevention of contamination of many medical instruments such as Gastroscopes, Colonoscopes, Sigmoidoscopes, Cholangioscopes, Trans Esophageal Echocardiogram probes, Cystoscopes and many similar units. This unit introduces a combination of covers that are made from latex that will be used to cover the body and shaft part of the endoscope as well as the other areas and pieces that are commonly contaminated by the user. So that putting all these together, the unit will be covered by a layer of latex all over, which will protect the unit from being contaminated.

Understandably, when the units are less contaminated, then it would not be necessary to clean them as hard. The fact that these units will need less cleaning will cause less wear and tear and may prolong the life of these very expensive units. Also the potential contamination of patients with toxic cleaning materials used to disinfect these units will also be much less. These units will be made for all the similar types of endoscopes with minor modifications to allow them to be used safely.

BRIEF DESCRIPTION OF THE DRAWINGS

FIG. 1 is a side view, partly in section, of a stethoscope.

FIG. 2 is a right hand view of FIG. 1.

FIG. 3 is a fragmentary view similar to FIG. 1 of a modified form.

FIG. 4 is left hand view of FIG. 3.

FIGS. 9-12 are views of different covers for fitting onto patient-engaging portions of instruments.

FIG. 13 is a bottom view of FIG. 12.

FIG. 14 is a view like FIG. 12 showing a modified form.

FIG. 23-25 are views of covers with bumps.

DETAILED DESCRIPTION OF THE DRAWINGS

Figure 5:
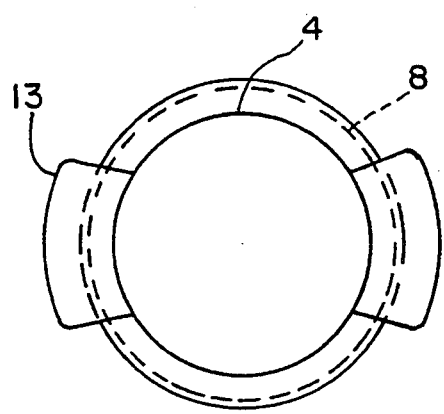
FIG. 5 is a view similar to FIG. 4 of another modified form.

FIGS. 1 and 2 show a stethoscope having both diaphragms 1,2 covered by protective covers 3, 6. Each cover has gone over the edge of its diaphragm and is placed in the back of the unit and also has a stronger rim in the end to hold it in place tightly. The rim of the diaphragm is shown by 8. The end of the tube of the stethoscope connects to a base 5. The elastic rims are shown by 4 and 7.

FIGS. 3 and 4 show a large diaphragm 1 covered by a cover 3 which has a tab, or tongue, 9 in its rim. This tab will allow easy placement of the cover on the diaphragm. The piece of base 5 connecting to diaphragm 1 is shown by 10. The outer rim of the cover is 11 and the elastic inner rim is 4.

Figure 6:
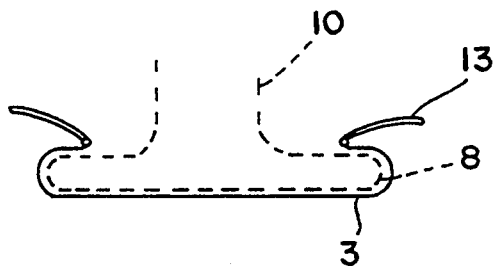
FIG. 6 is bottom view of FIG. 5.

FIGS. 5 and 6 show a cover for the large diaphragm with two tabs 13 and a shorter rim 4 for the back.

Figure 7:
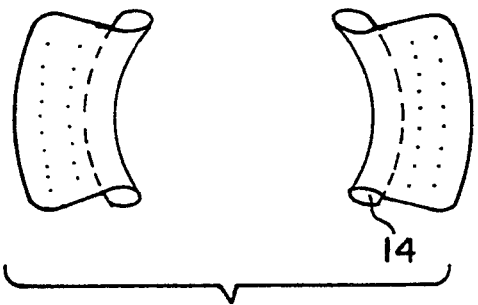
FIGS. 7 and 8 are front and bottom views of an accessory for installing a cover.
Figure 8:
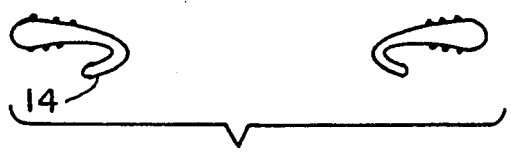

FIGS. 7 and 8 show plastic pieces 14 that will help in placement of a cover when it does not have a tab.

Figure 9:
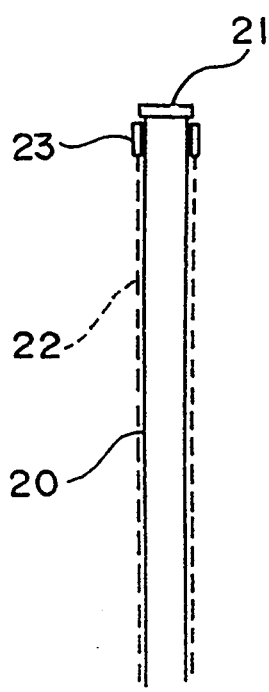

FIG. 9 shows a shaft 20 of a scope unit that has a cover 22 on it. Close to the tip 21 of shaft 20 is a rim of thicker latex 23 in order to hold this cover in place tightly and prevent it from being pulled back with manipulation which can be destructive in imaging.

Figure 10:
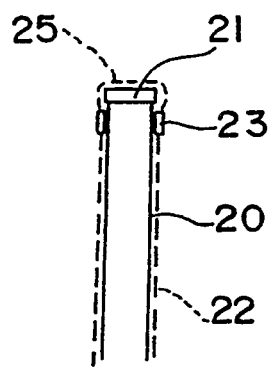

FIG. 10 is like FIG. 9 except that the tip 21 is covered by the cover itself at 25. This version is to be used with units, such as Trans Esophageal Echocardiogram, or rectal and vaginal ultrasound transducer units, that do not need an opening in the end.

Figure 11:
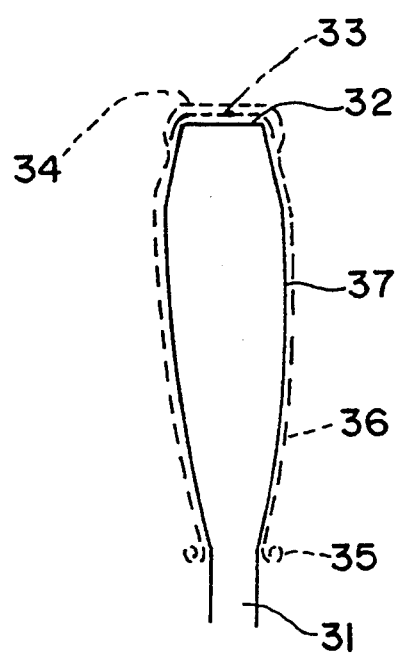

FIG. 11 shows a unit that is to be used with the tip of the transducers. This cover has a matching shape and will be rolled on the transducer, and it has a layer of gel on it. The tip of the transducer is shown by 32, the body of the transducer by 37, the base of the transducer by 31, the body of the cover by 36, and the tip by 34. The rim of this cover is shown by 35 and importantly it is round and thick and elastic to facilitate the movement of the cover in and out from the transducer. The gel is shown by 33.

FIGS. 12 and 13 show a unit that is very similar to the one shown in FIG. 11 except this unit has tabs 40, 42, 43 that will allow the unit to be pulled over the tip of the transducer easily. The rim of this cover is shown by 39 and it is soft and not as thick as the previous model.

FIG. 14 shows a unit that is very similar to the one shown in FIG. 11 except this unit has small raised spots S of latex on its surface that will give a better traction for the unit when it needs to be rolled away and also will give a better grip for the user and better feeling to the technician.

Figure 15:
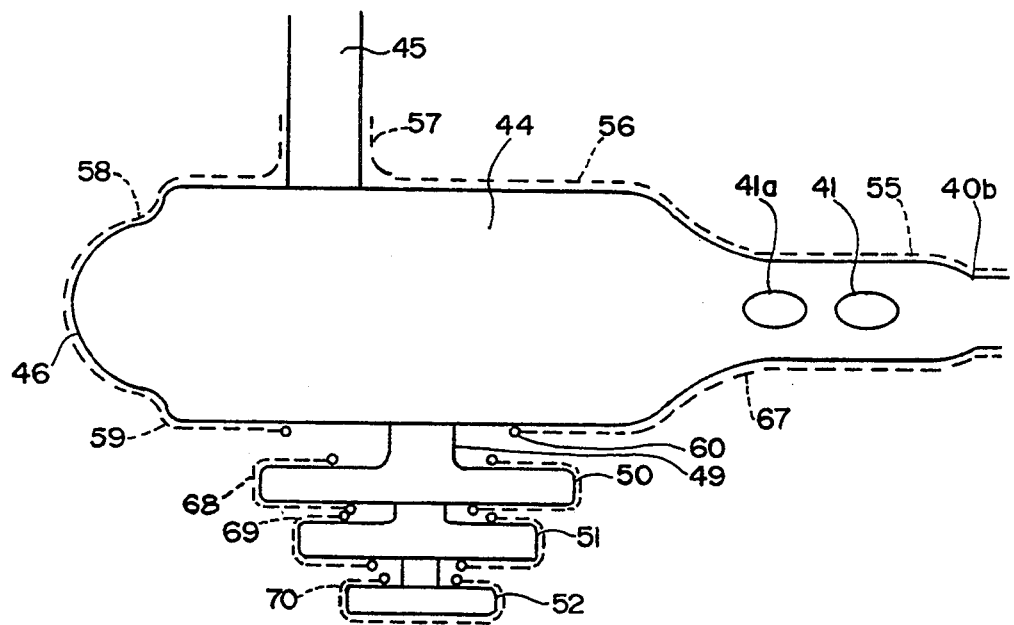
FIGS. 15 and 16 are top and rear views of an endoscope with the inventive covering system.
Figure 16:
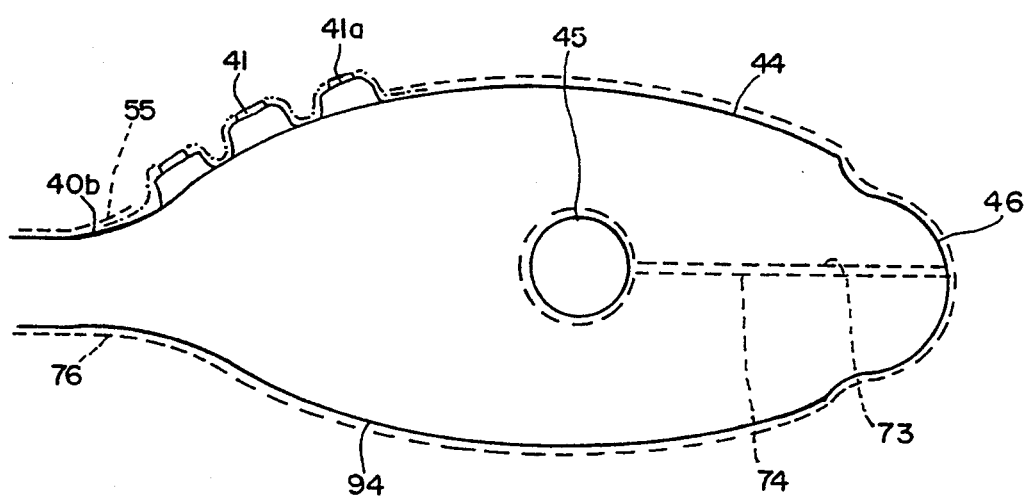

FIGS. 15 and 16 show combinations of covers that are covering the body of a Gastroscope or a Colonoscope unit or a similar type of endoscope. The body of the unit is shown by 44, its rear part by 46, and the base of the shaft by 40b. This unit connects to a computer compartment by a cable 45. The direction of the tip of the shaft of this scope is usually done by control knobs here shown by three knobs 50, 51, and 52. The knob 51 is connected by an axle 49 to the body of the scope. Numerals 41a and 41 show the base of the two common buttons on the top surface of the body of the scope which are for suctioning and similar function. Please be advised that the walls and parts of this unit are shown by a solid line, while the cover is shown by a dotted line that is covering the body of the scope and its components. Here the cover comes from the base 40b of the shaft and continues its way (55, 56, 76, 67) to come and go around the cable at 57 and then to cover the rear part 46 at 58 and also it covers the base of the control knobs (59, 60). In the place of the control knobs the cover goes around the knobs and covers the sides that are likely to be contaminated. In FIG. 15 the piece 68 covers the knob 50, the piece 69 covers the knob 51, and the piece 70 covers the knob 52. The no. 60 shows a thickened piece of cover which stands on the body of unit at the base of the knobs.

FIG. 16 shows the top of the unit by 44, the bottom part by 94, and edges that come and stand next to each other along lines 73 and 74.

Figure 17:
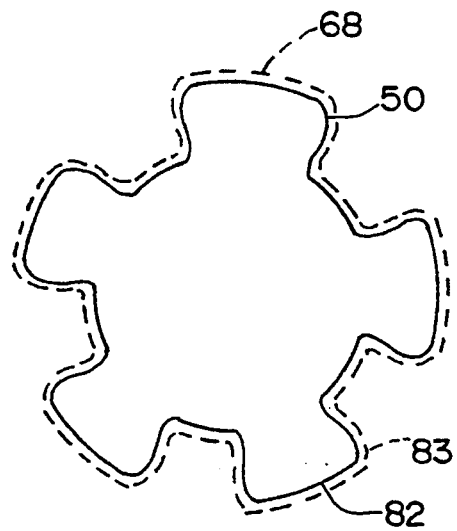
FIGS. 17-21 are views of various portions of the inventive covering system relating to the endoscope control knobs.
Figure 18:
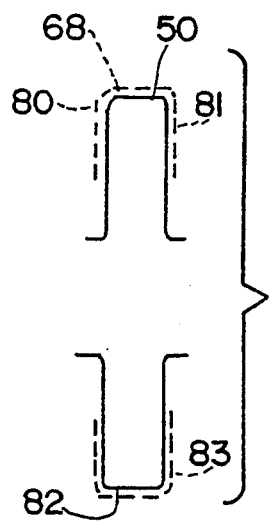

FIGS. 17 and 18 show control knob 50 that is covered by cover 68. In the lower side, one of the sides of the control knob is shown by 82 with cover part 83 covering it. The cover also has parts shown by dotted lines 80, 68, and 81 in the top.

Figure 19:
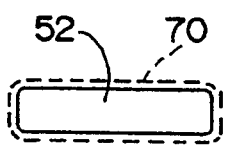
Figure 20:
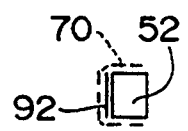
Figure 21:
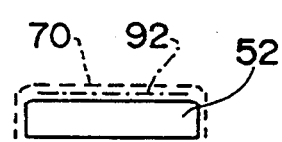

FIGS. 19-21 show control knob 52, covered by cover 70, which will be fitted on its outer surface. A small layer of glue 92 holds them together, as well as the shape of the cover which fits the knob right.

Figure 22:
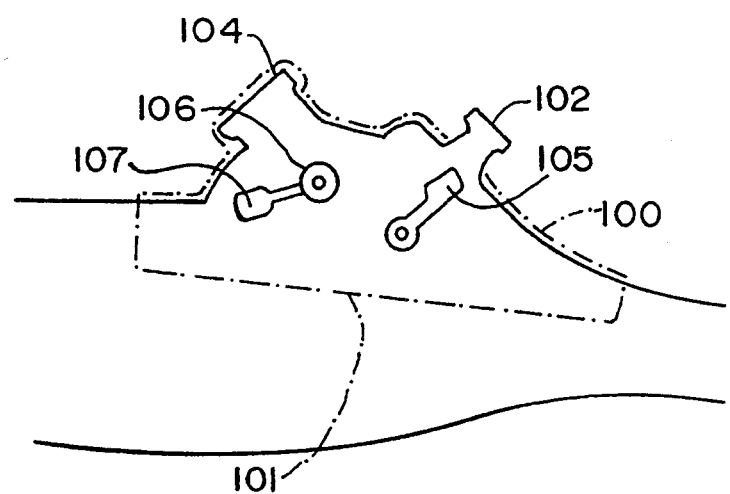
FIG. 22 is a view of a further cover portion for endoscope controls.

FIG. 22 shows the part of the body of the scope that is located between the body itself and the shaft 40. In this part and in some models few knobs and openings and some control handles are located. Here a small cover 100, 101 shown with a dash and dot line goes and stands on the base of these pieces to cover the intended spots and places, such as 104. This cover may be made from hard clear thin plastic, with openings such as around 102, 106 to let the handles 107, 105 be left out to be covered by small covers of their own. These small covers will match the handle's shape and will be pulled or pushed on the handles to do the job.

FIGS. 23 and 24 show a shaft 20 of a unit that has a cover 140 that is being pulled on it. The cover has special raised areas 141 that will give better and more traction to the cover and will facilitate the placement in and out of the unit. Also importantly, this unit has a soft but solid piece of elastic 142 inside that is like a doughnut, and this is to make the job of rolling the cover much easier since very importantly it will give a much better grip especially when the person has a touch of arthritis in the hand and in conditions where the surface can be slippery due to secretions and contaminations and a small piece may not be as helpful and functional to be moved without significant difficulty and causing significant contamination. The tip of shaft 20 is shown by 21 and the thicker tip of the cover by 23. The rolled cover is shown by 143. This fig. shows how the cover can be rolled back and forth easily and the thicker part of the cover is to prevent motion of the tip of the cover back and forth.

FIG. 25 shows a shaft of a unit that has a cover pulled on it, very similar to the one shown in previous two figures except the tip of this cover has special shape shown by A so that its edge has turned to go over the corner of the tip of the shaft shown by 21. This special construction will prevent the cover to be pulled back and forth. This piece is fortified and may be made from harder plastic or elastic piece.

Figure 26:
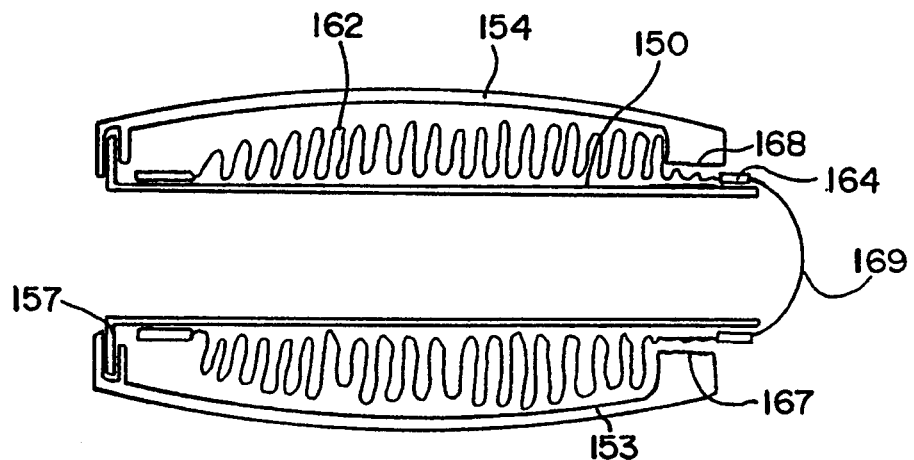
FIG. 26 is a view of an installation tool.
Figure 27:
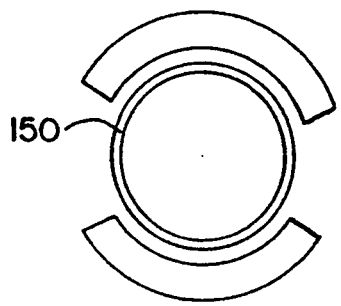
FIGS. 27-29 are views of various other accessories that facilitate cover installation.

FIGS. 26 and 27 show a delivery system that is to facilitate the placement of the cover on the shaft. This unit has a central piece that is made from a rigid or semi-rigid center tube 150 that is slightly larger than the shaft of the unit with which it is to be used so that it can be pulled over the shaft easily without scratching the surface of the shaft. The inner cover of this piece will be also soft enough not to scratch the outer layer of the shaft. The cover 162 will be pulled over this center piece and will be compressed on it and stay there until it is released. The tip of this cover 169 is shown and the thicker piece 164 may be also held on the tip of this central tube. The base of this central tube has a raised wall 157 that will allow the placement and connection of the base of two control pieces 154 and 153. These pieces each has a front end with soft teeth 168, 167 that will press the cover and can hold it tight against the wall of the central tube in that area so that the cover cannot be released when these pieces are pressed. This method will provide a means of controlling the release of the cover, which can be intermittent, so that the person will pull this unit and can keep the cover released to allow it to be moved and to cause tension when it is pulled without releasing the cover. The outside surface of these handles may have a shape and surface to allow holding them easily by the hand. When the cover is pulled on the shaft at the end, these handles can be separated from the unit by removing them from the base of the central tube. Some spring type function may be given to these handles to allow a better function. The shaft cover will have appropriate markings or coloring on its surface to indicate the length of the released parts.

This method will prevent the cover from being pulled more or less than the right amount and causing possible problem with weakening the wall of the cover, since if the cover is pulled hard, it will weaken the wall and cause microscopic tears. If it is not pulled enough, it has to be pulled more later to compensate for the length.

Figure 28:
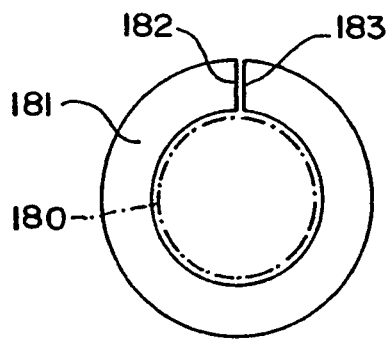
Figure 29:
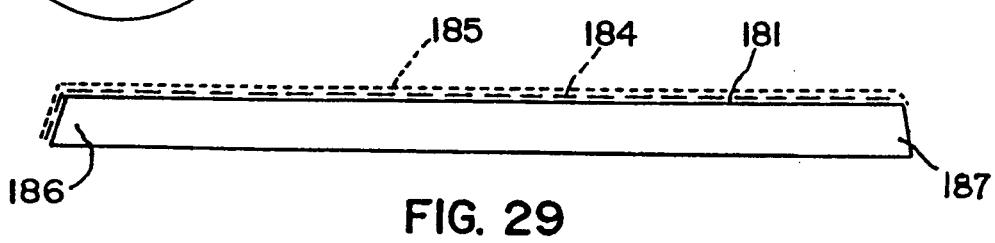

FIGS. 28 and 29 show an elastic piece 181 that is to be stuck over the cover in order to allow it to be rolled back easily. FIG. 28 shows this unit wrapped over a cover shown by dot and dash line 180. The ends of piece 181 are shown by 182, 183, stuck to each other.

One surface of piece 181 contains an adhesive layer 184 that is protected by a removable clear plastic layer 185 that is to be stuck around the cover around the shaft and give the means of letting it to be rolled away. At the time of use the clear plastic cover will be removed, then the adhesive surface will be stuck on the surface of the cover all around to let a ring or doughnut to be made similar to FIG. 28. Then the cover is rolled away. The adhesive layer 184 extends to one end 186 so that, that end will be stuck to the other end 187.

Figure 30:
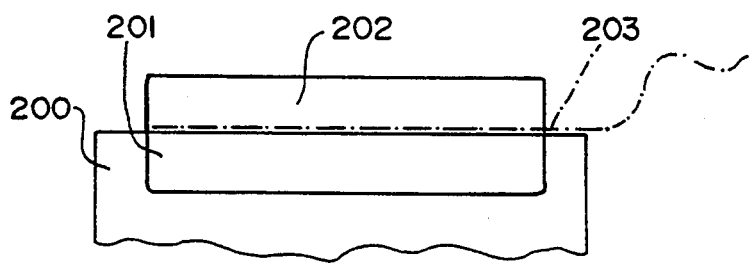
FIGS. 30 and 31 are views relating to a tear strip for removing a cover after use.
Figure 31:
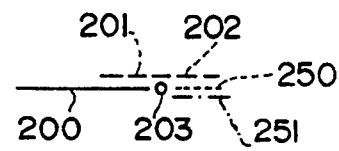

FIGS. 30 and 31 show a piece of latex 200 that has a cover of adhesive paper 201 on it. This adhesive paper is sticking along one side to the latex layer and along its other side 202 has a layer of adhesive 250 on its surface that is covered by a plastic layer 251 that is removed to allow it (202) to stick to the surface of the other latex layer. This piece has a thread 203 that will tear its overlaying paper when it is pulled to allow it to be removed easily. At the time of use, the plastic cover layer 251 will be removed to allow the adhesive piece to stick to the other side of the latex.

Figure 32:
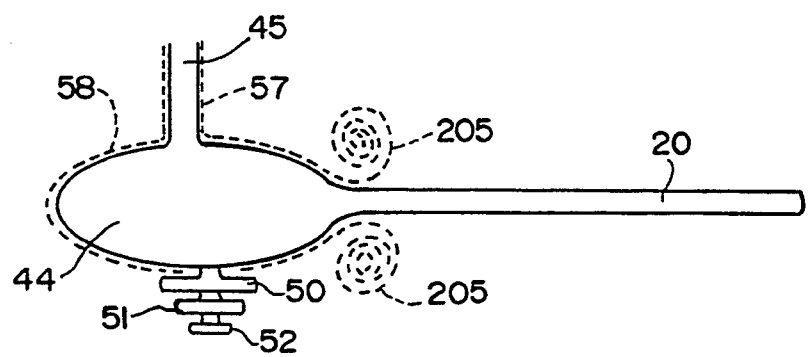
FIGS. 32 and 33 show various aspects of cover installation.

FIG. 32 shows a scope that is being covered by a cover unit where the body of the cover for the shaft is rolled up at the base of the shaft ready to be pulled over the shaft. The body of the unit is shown by 44, with its rear part covered by 58 and the base of the cable by 45 and the cable cover by 57. The control knobs are shown at 50, 51, and 52. The rolled-up cover for the shaft 20 is shown by 205. This cover will be then rolled on the shaft to cover it to the end. At times when the unit is long, it will be cut to size and a band of tight latex will be used to hold it in place at the tip.

Figure 33:
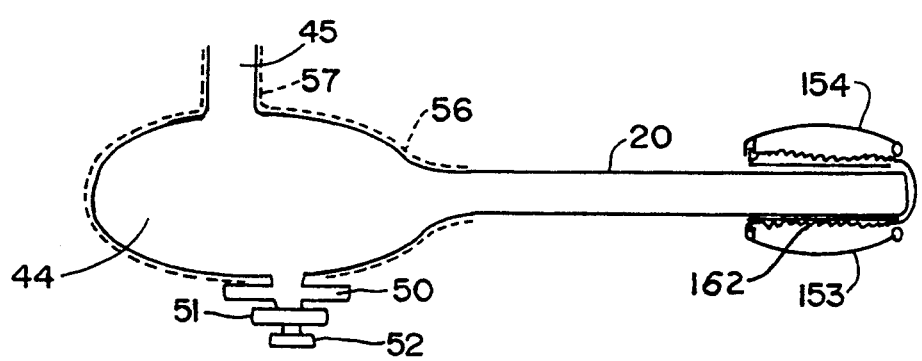

FIG. 33 shows a scope whose body has been covered by a body cover 56, 57. And the shaft cover is in place at the tip and ready to be pulled back to the base of the shaft by the delivery system of FIG. 26. The body of the unit is shown by 44, and the base of cable that goes to the computer compartment by 45. The control knobs are shown 50, 51, and 52, the shaft is marked by 20, and the cover 162 for the shaft is shown ready to be placed by the delivery system whose control pieces are unit shown by 154 and 153. The delivery system will be pulled toward the body of the unit to cover the shaft all along, and then the handles will be removed.

Figure 34:
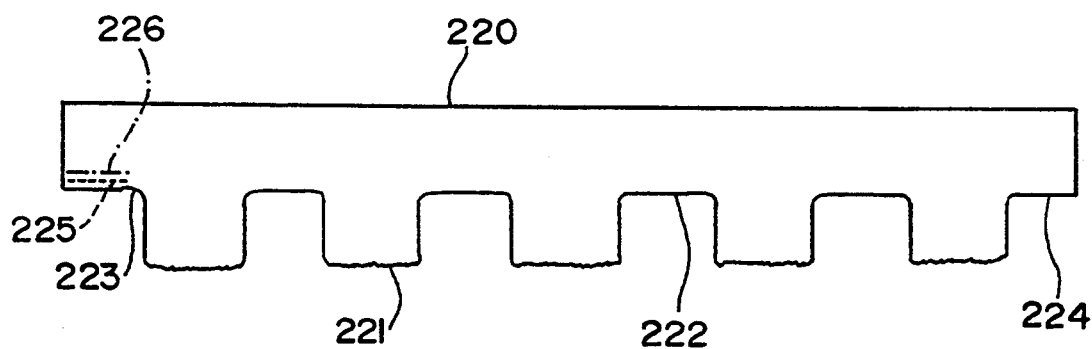
FIGS. 34-36 relates to further forms of knob covers.
Figures 35, 36:
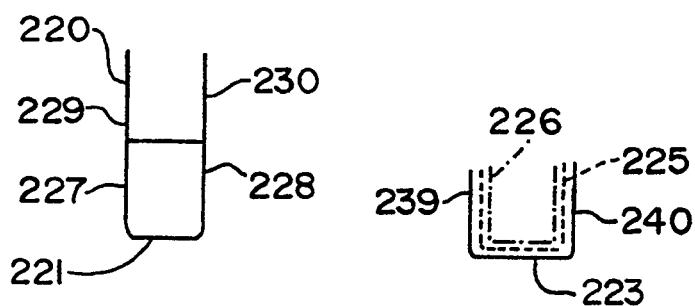

FIGS. 34-36 show a cover that is designed to cover the knobs 50, 51. This cover will be also made from latex and will have a shape that will be slightly tight (in order to stay in place) on the surface of the knob. This piece will be pulled over the knob to come in one point and to stick on the outer surface of the other end. The rim of this unit is shown by 220. Please notice that in practice this rim will be in circle shape. The piece that goes on the raised part of the knob 50 is shown by 221, the piece in-between those is shown by 222. The end of this cover which does not have adhesive surface is shown by 224; the other end that has a surface covered by small area of glue by 223. The adhesive is shown by 225 with a removable plastic cover shown by 226.

FIG. 35 shows the side view of a cover. The piece that goes to the raised part of the knob is shown by 221, one side of this piece by 228, and another side of it by 227. The rim of the side that goes to the base of the knob is shown by 220 and its sides by 229 and 230.

FIG. 36 shows the side view of one end of the cover that has the adhesive on its inner surface. The outside surface of this part is shown by 223, then one side by 239, and the other side by 240. The adhesive is shown by a dotted line 225, and the removable protective plastic cover by 226.

DETAILED EXPLANATION OF THIS INVENTION

The need for complete sterility of the instruments used in medicine is now more obvious and many times mandatory. This issue has a physical as well as psychological aspect. There are many people who live a clean life and do not want to have a unit that was used in the other patients to be inserted bare inside their body even after cleaning. The reason is that germs such as AIDs virus are extremely small and cannot be seen even by microscopes and the cleaning of these instruments by humans is subject to human error and cannot be controlled by human eye. So prevention of such psychological concern is of significant importance in the inventor's mind. It is always better to avoid and prevent psychological worries and fears than to use medications afterward to control them. In this case one bottle of nerve medications to suppress the worries of patients will cost many times more than the price of a cover. Considering these facts this unit is introduced for usage in scopes such as gastroscope, colonoscopes, or similar ultrasound units.

Stethoscopes

In the same subject let's also consider stethoscopes and their function. As we can imagine, stethoscopes are used in many conditions in patients who have cuts, bleeding and wet secretions from different areas of their body, and body fluids of any kind on them. While they may not be seen when they are wiped off by patients or medical staff, millions or uncountable numbers of microscopic germs remain in place. So the user will be unaware that many times his or her stethoscope touches dirty skins of such patients and then carries them from one patient to another. Even if someone notes this in general, stethoscopes are not made to be washed and be washed routinely, and even the facilities for washing and soap and towels are not available every time, and washing would be very expensive if were available. Therefore in my opinion at very least in certain areas such as Emergency Room and certain patients such as AIDs patients, or patients with wet surfaces especially, the diaphragm of stethoscopes should be covered and cover be changed, similar to the gloves of the examiners. Ideally it will be part of best practice to change from one patient to another for the same reason we change the cover of the exam tables and pillows. The same consideration is also true about use of transducers of the ultrasound and the scopes that are being entered into the body of a person. It will be very wise and a very valuable service to patients to use in all such cases disposable covers that will prevent contamination to a great degree.

Having this background in mind this application is about covers used for medical instruments particularly the stethoscopes and transducers and endoscopes. The basic cover will be made from latex or similar material to be used for covering such medical instruments that touch patients and can be contaminated. This cover will have a shape and size and construction to allow it to be pulled and to cover the areas that turn out to be contaminated at the time of use with a patient.

In its simplest form this unit has a shape of a diaphragm of a stethoscope, and will be pulled over both the small and larger diaphragms. It will be made from latex that has a front part that will fit the diaphragm and a rim that will be pulled over the edge of the diaphragm area of the stethoscopes and to stay in its back. In order to make this job easier the cover may have a piece in shape of a tab or tongue to facilitate pulling the cover on the diaphragm. The rim of this cover will be a thicker part to act like a rubber band. Importantly some models may be made to go over the metal part of the tip of stethoscopes so that the need for diaphragm will be eliminated and the unit will be cheaper to produce. So these units will use disposable covers that are thick enough to go over the tip of stethoscopes and be used and then to be thrown away.

Importantly another model may be made that is longer and has a bigger piece that will fit the large diaphragm and a smaller piece in the other end to be pulled and go on the smaller diaphragm so that only one piece covers both of them and makes the function of pulling easier and simpler if someone intends to use both diaphragms.

Cover for the Tip of Transducers

In the case of ultrasonic transducers it is also wise to consider that in practice these are to be pressed and rubbed against skin when the skin is covered by the gels. This is an unsafe practice, at least it may bring a question to mind of many patients that maybe they will get AIDs or other diseases by rubbing a probe that is used on thousands of other unknown patients and can be contaminated by many unknown germs. For prevention of such very annoying and disturbing thoughts and problems, the tip of such transducers of ultrasounds will be covered by utilizing the same technique. And basically this will be a cover made from latex layer or a thin plastic that has a matching shape to fit and be pulled or rolled over the transducers of the ultrasounds. This piece also may have tabs or tongues in its end to allow the unit to be pulled over the tip of the ultrasound transducer units. If this is made from clear plastic rather than latex then it is usually best to be pulled. However the latex units are to be pulled and rolled as well. In the case of ultrasound transducers, the inside surface of the tip of these covers may have a layer of gel covered by a protective plastic to be removed before being placed on the transducer. Also sometimes it may be helpful to use gel in order to facilitate the pulling of the cover on the shaft.

The Cover for Endoscopes and Similar Units

The technique for covering the scopes also uses covers made from latex or plastic or their combinations, which will be shaped to make a cover for many of the medical instruments such as Gastroscope, Colonoscopes, Sigmoidoscopes, Cholangioscopes, Trans Esophageal Echocardiogram probes, Trans rectal and trans vaginal ultrasound probes and Cystoscopes and the other similar units. These instruments basically have a long tubular shaft that is inserted inside the body, to be then turned or bent to different directions by using control knobs located on the body of the unit.

The long piece of these units here referred to as "shafts" has means of lighting the tip of the shaft and it also has a flushing system as well as a hole inside that is for snares to be inserted to cut and remove small particles through them. The body of the unit has in some models a small viewing window to look through the shaft, however in larger models the body does not have the viewing window since it is connected to the light source or a computer compartment by a thick cable. So in order to cover the whole unit this application introduces a cover that has three basic components to cover different parts, and these are as follows:

1. A piece to cover the body.

This will be made from a layer of latex that will have a shape to match the outside of the body of the scope and allow it to be pulled easily over the body to fit comfortably on the body and to be pulled against its wall. The latex may have raised lines or spots so as to give a nice grip to the cover. When this unit is pulled at some opening it will go over smaller pieces that are placed to cover opening of some buttons or other openings. Then the cover will be pulled all along and in its way one side of it will stand in the base of the control knobs and then to be pulled to the rear end of the body of the instrument to wrap around it and to come together in the other side. The edges of this cover will overlap and will be closed by use of glues or adhesive tapes or a special adhesive tape, to leave no place for contamination. Considering the fact that the unit may have an object window for viewing or be connected to the computer technique, then two kinds of body cover will be made as follows:

a. The kind that has an objective piece like the eye piece of a binocular, in which case the cover of the body will have a separate piece that will fit easily on this piece and then the rear end of body cover itself will end at the base of this part, and its rim will have a thick part that will function like an elastic band to hold the end of the cover tight and secure in place and to prevent tearing of the rim of the cover as well.

b. The kind that is a larger, more expensive unit that utilizes the computer compartment for viewing. This unit shown in FIG. 15 has a cable that is connected to the left side of the body. In such cases the cover will be made to go around it and to turn and come around the cable and to be stuck to each other. The cable itself will be covered either by wrapping a suitable cover or rolling a unit coming from its connection plug toward the base, or vice versa, using a unit similar to the model which is explained for the shaft.

Each of these covers may have a connection to the piece that is to cover the shaft, and importantly the body cover may use bands or rings of elastic or thickened latex or rubber that are to hold the cover in place. The body of this unit may have small spots or lines of different shapes of raised areas of latex to give a better traction to the unit which is to function like the treads of tires. Importantly the unit will have markings, and shapes and figures outside, as well as different coloring and printings of directions and signals, etc. to allow the person to identify the underlying covered areas and to make the use as much easier and likeable as possible.

Importantly the latex may have different thickness in different areas in order to serve different purposes; for example in the base, in the edges and in connection areas, it may have a thicker layer.

Also importantly combinations of latex and clear plastic will be also used to allow the visibility to be maintained in some areas where it is necessary or will be helpful to recognize the underlying pieces. So in such cases the visibility will be provided by the clear plastic and the coverage and elasticity to be delivered by the latex layer. The importance of function of such windows is clear since it will allow precise functioning.

Also importantly pieces of rigid plastic in shape of lines or surfaces may be used whenever there is a need for a firm frame or surface to make or maintain a shape so as to allow making the placement and use of such units the best and most convenient.

Alternatively a body cover also made from somewhat rigid clear plastic holds the body of the unit inside itself like a case which may be easy to be placed in some models of the scopes.

2. The piece for covering the shaft.

This piece will be made from a tubular latex with a shape and size to match the size of the shaft in order to go over the shaft of the scope. This piece will have an open end for units that are to use light source as well as open end for the snare and flushing system. In these models the cover will have an open end; however importantly the tip of this cover will have a circular piece made from hard plastic or thick latex or rubber that is to match and stand tight and secure on the tip of shaft of scopes and prevent its displacement back and forth either way.

In cases where the end does not need to be open, such as ultrasonic scopes, then the end of the cover will be closed and may have a layer of gel in its tip to prevent pockets of air from standing between the inner surface of the tip of the cover and the tip of the transducer in the shaft. These cover units will have a tight fitting around the tip of transducer to prevent presence of air pockets in that area. And they may have a tight band of latex above the transducer tip to hold the gel in place.

Importantly the connection areas between the cover of the shaft and the body and other connection areas will be done skillfully so that these areas will match each other's size and shape and they may also have areas of adhesive to allow a secure and stable connection to be done as well as to make them waterproof when needed. Adhesive tapes and bands may also be used for this purpose.

The Methods of Placement of the Covers on the Shafts

At the time of use, the end piece of these units will be placed at the end of the shaft to stay there securely due to its size and construction as mentioned (which matches the size and will fit the tip tight and stay there). Then the rest of the shaft cover is to be pulled or rolled over the shaft. This will be done by two methods:

1. The pulling method.

In this method the cover of the shaft will be pulled over on the shaft with use of a specially designed delivery system to make the pulling job more easily possible, accurate and comfortable. This delivery system consists of a rigid or semi-rigid center tube that is slightly larger than the shaft of the scope so that it can be pulled over the shaft easily without scratching the surface of the shaft of the unit. The cover will be made and pulled on this part to stand compressed on the surface of the center tube and to stay there until it is released. At the time of use, this unit will be pulled over the shaft after first the end piece of the cover is placed and secured on the tip of the shaft of the scope and then the shaft cover will be pulled toward the base of the scope while the handles or forks are released to permit slow and even release of the cover to stand on the shaft under it. The shaft cover has markings on its surface showing the length. Sometimes it may be helpful to use gel in order to facilitate the pulling of the cover on the shaft. As mentioned earlier this is important since otherwise the cover will be pulled more or less than it should be to cause possible problem with the cover, since if the cover is pulled hard, it will weaken the wall, and if it is not pulled enough, it has to compensate later to eventually cause some other part to be pulled more to compensate for the loss.

2. The rolling method.

In this model the shaft cover is designed to be rolled up toward the base of the scope after the tip of the cover is placed appropriately, and the end tip which will be similar to the kind mentioned earlier to be placed and secured at the tip of the scope. Importantly the cover of shaft in this case may also have small spots or different shaped lines (in one or both in and out surfaces) of raised latex in order to give a better grip and traction to the cover for better use: placement as well as removal; again something similar to function of the treads of tires. The rolling will be continued until the whole shaft is covered.

It is to be mentioned that the contact areas between the body cover and the shaft cover will be tight and the contact between these parts will leave no openings, and if necessary then, a piece of adhesive tape or latex will be used to make this connection area strong and fully covered.

The Cover for the Cable

The cable that connects the body of the scope to the electronic computer piece and plugs into the computer, is usually much less contaminated. This piece may be also covered by a cover that can be rolled on it. Or alternatively, this cover may be made from a piece to be wrapped on the cable and to have an adhesive tape to hold the sides together. In order to allow this wrapping to be removed easily after use, then the adhesive tape will be made from a piece of stronger paper, with a thread in its wall that has a part that has adhesive layer protected by a removable plastic cover that will be removed at the time of use to expose the adhesive part to stick to the surface of the other side of the wrap (FIGS. 30 and 31). At the time of removal, the thread will be pulled to tear the cover and allow the cover to be easily removed.

The System for Covering the Knobs

The technique designed for covering different knobs of this unit are as follows. First from my observation basically there are following groups of buttons:

1. The knobs and buttons on the top surface of the body that are to be used for suctioning, flushing, and snaring, etc. These buttons will be covered first by a small cap made from a hard clear thin plastic that will have a matching size to allow the piece to be situated on the place easily. Then after placement these can be held in place with use of latex, although they may have a thin band of elastic of their own to go around the body to be held in place. The cover of the body will be pulled on this part to hold it in place.

Alternatively and importantly the cover piece for these buttons may be made from combinations of latex or clear plastic in the center and hard plastic around it so that the latex or clear plastic part can be pressed to allow the underlying button to function; if there is a hole on the button then a hole also will be made in this cover as well.

2. The control knobs on the right side are to be covered by a special latex or clear plastic covers that will be pulled on them to be held on place, securely due to their shape and elasticity of the latex. Small tabs on the surface of this cover will help in their placement. Alternatively the cover for each one can be totally separate to allow piece-by-piece placement of these units to be done. So the first two knobs 50 and 51 will be covered by covers that are shown in FIGS. 17–18.

The pieces for the knobs may also be made from a layer of plastic that is like a cradle for them and will be placed on one side to go around them and to come and stick to its end from the other end (FIGS. 34–36). Or they can be like a matching cover that will be pushed against the outer surface of the knob to stand in outer side of it, due to its shape and slightly tight size, as well as use of small removable adhesive to help in this purpose.

3. The very external control knob 52 which is in the center of right side control knobs will have a special cover of its own shown in FIGS. 19–21. This cover will be made from a hard plastic that will fit this knob tightly and be kept in place by the shape of this piece that will fit on the knob tightly. Also a small spot of removable glue (similar to the one in back of some note pads) may be used to keep it in place. Also combinations of soft and hard cover will be used to hold it in place with or without use of adhesive.

4. There are small knobs specified in units as lever f which is a small flat knob of 4–5 mm width by 1 mm thickness that can be covered easily by a small latex cover or a hard plastic cover that will be pushed to go over it; a small piece of latex may also be placed on it by help of a piece of hard plastic that will be fitted in place.

5. Cover for the ocular pieces.

As mentioned earlier some of the scopes have an ocular pieces for observation, that will be covered by a piece that will be pulled on the surface of the ocular piece easily. This will be made either from latex or a hard plastic piece, and would match its shape and would be easily placed on it. Since this is a separate piece it would allow the ocular piece to be easily rotated.

Importantly a piece of clear plastic in center surrounded by latex layer may be used to cover the buttons or other pieces of these covers, so that the clear plastic will allow visualization of the underlying pieces to be done with benefit from the latex layer to pull the cover and hold it in place.

Combinations of these units will allow the total coverage of the body of a scope, its shaft and the cable and knobs to be done that although not 100%, will truly be the best cover in the inventor's mind to cover the whole area which in practice comes in contact with user and there has reasonable chance to be contaminated, and although the exact details of different covers for every model are not explained in this application. However, since these units, scopes, etc. are very similar, it is sincerely believed that the method mentioned here with only minor modification can be used in other models as well. Benefit of use of such unit should be compared with the units that are cleaned by nurses, and subject to human error many times.

The Advantages of these Covers

In order to emphasize the advantages of such covers, they will be mentioned here.

1. The most important role of these units is to prevent transmission of germs from one person to another. I do not know of any unit or system that can be this much protection.
2. The other important role of these covers is to prevent contamination of the units when they are used on human beings.
3. Another very important role of these units is to give the sense of security to those patients that are aware of problems with the present methods, so that very importantly, the group of people who suffer from problems and do not want those scopes to be used on them will feel safe enough to accept the procedure.
4. These units may decrease the time used by nursing staff for cleaning of the units.
5. These units may decrease the use and expense of the chemicals used for cleaning of such units.
6. These units will eliminate the contact of potentially toxic materials that may remain on the surface of the scopes after washing.
7. These units may practically eliminate the chance of legal problems that may arise from use of bare equipments in certain cases.
8. These units may decrease the chance of wear and tear in these expensive equipments.

At the time of use these covers will be delivered in sterile condition so that they can be pulled over the units in sterile fashion. The body cover will be pulled and the shaft cover and the other covers will be placed. The connection points will be covered by pieces of adhesive tapes with thread or pieces of appropriate latex pieces, so that the whole scope will be covered safely. After the time of use, the unit can be washed to have the visible contaminated materials removed, and then to be dried by paper towels, and then to have the covers removed one by one, so that the chance of contamination can be very significantly diminished.

I claim:

1. A cover system for an endoscope comprising a control head having controls for operating the endoscope, and a shaft extending from said control head and having a patient-engaging portion spaced from said head for invading a patient's body under the control of said control head, said cover system comprising: a first elastomeric cover portion adapted to be disposed in covering relation to at least a portion of said patient-engaging portion so that said first cover portion prevents said portion of said patient-engaging portion that it covers from having direct contact with a patient, and further including a second elastomeric cover portion adapted to be disposed in covering relation over at least some of said control head, and a clear plastic cover adapted to be disposed in covering relation over a portion of said control head.

2. A cover system for an endoscope as set forth in claim 1 in which said first cover portion has a distal end that is adapted to be disposed over a distal end of said shaft, and a small hard piece of plastic is disposed over said distal end of said first cover portion to fit tightly onto said shaft and thereby hold the distal end of said first cover portion in place on said shaft.

3. A cover system for an endoscope as set forth in claim 1 in which said first cover portion has a distal end that is adapted to be disposed over a distal end of said shaft, and has a strong elastic band to hold itself in place on said shaft.

4. A cover system for an endoscope as set forth in claim 1 including a delivery system for delivering the first cover portion onto the shaft comprising a central plastic tube slightly larger than said shaft for holding the first cover portion and handles on said tube for selectively engaging the first cover portion to enable the first cover portion to be pulled a desired amount over the shaft.

5. A cover system for an endoscope as set forth in claim 1 in which said first cover portion is rolled onto and off of the shaft and includes length markings that facilitate such rolling.

6. A cover system for an endoscope as set forth in claim 1 in which at least one of said elastomeric cover portions includes tabs that facilitate its installation on an endoscope.

7. A cover system for an endoscope as set forth in claim 1 in which at least one of said elastomeric cover portions is constructed and arranged to be rolled onto and off of an endoscope.

8. A cover system for an endoscope as set forth in claim 1 including a gel layer that facilitates installation of at least one of said elastomeric cover portions on an endoscope.

9. A cover system for an endoscope as set forth in claim 1 in at least one of said elastomeric cover portions is constructed and arranged to be rolled onto and off of the endoscope and includes bumps that facilitate such rolling.

10. A cover system for an endoscope as set forth in claim 1 in which at least one of said elastomeric cover portions is constructed and arranged to be rolled onto and off of the endoscope and including a piece of elastic disposed on said one cover portion that facilitates such rolling.

11. A cover system for an endoscope as set forth in claim 10 in which said piece of elastic is a separate piece that is stuck on said first cover portion.

12. A cover system for an endoscope comprising a non-patient-engaging portion including a control head having controls for operating the endoscope, and a shaft extending from said control head and having a patient-engaging portion spaced from said head for invading a patient's body, said cover system comprising: a first elastomeric cover portion adapted to be disposed in covering relation to at least a portion of said patient-engaging portion so that said first cover portion prevents said portion of said patient-engaging portion that it covers from having direct contact with a patient, and further including a second elastomeric cover portion additional to the first cover portion adapted for covering a portion of said non-patient-engaging portion, said second cover portion comprising plural openings each providing access to a respective portion of said control head that it surrounds, and at least one further cover portion additional to said first and second cover portions adapted for covering at least a portion of a corresponding one of such surrounded portions of said control head.

13. A cover system for an endoscope as set forth in claim 12 in which said at least one further cover portion comprises a plastic cover portion adapted to be disposed in covering relation to at least some of said controls.

14. A cover system for an endoscope as set forth in claim 12 in which said at least one further cover portion is adapted to cover computer cables extending from the endoscope.

15. A cover system for an endoscope as set forth in claim 14 in which said at least one further cover portion comprises a strip that is adhered to said further cover portion to hold it wrapped around the cables and a string for tearing the strip after use of the endoscope so that said further cover portion can be removed from the cables.

16. A cover system for an endoscope as set forth in claim 12 in which said at least one further cover portion comprises a respective control knob cover adapted for covering one or more control knobs of said endoscope controls.

17. A cover system for an endoscope as set forth in claim 16 in which at least one of said control knob covers comprises a strip wrapped around the perimeter of the corresponding control knob.

18. A cover system for an endoscope as set forth in claim 17 in which said strip is held wrapped around the knob by adhesive means.

19. A cover system for an endoscope as set forth in claim 12 in which said at least one further cover portion comprises a transparent plastic cover for covering at least some of said controls while providing visibility for them.

20. A cover system for an endoscope as set forth in claim 12 including a piece of elastic stuck to one of said first and second cover portions in a circumferential sense around the outside thereof to facilitate rolling of said one cover portion on the endoscope.

21. A cover system for an endoscope as set forth in claim 12 in which said at least one further cover portion comprises a transparent cover adapted for covering an ocular piece of the control head.

22. A cover system for an endoscope as set forth in claim 12 in which said at least one further cover portion has an adhesive strip holding said at least one further cover portion wrapped around said non-patient-engaging portion and a string that allows tearing of the adhesive strip for removal of said at least one further cover portion from said non-patient-engaging portion.

23. A cover system for an endoscope as set forth in claim 12 in which said first elastomeric cover portion comprises a transverse elastomeric wall portion adapted to be disposed in full covering relation to a transverse distal end of the shaft.

24. A cover system for an endoscope as set forth in claim 12 in which said first and second cover portions come together and match each other, and an adhesive means secures said first and second cover portions together to form a leak-proof connection where the first and second cover portions come together.

25. A cover system for an endoscope that has a control head having controls and a shaft extending from said control head, said cover system comprising cover portions for said endoscope adapted for covering at least portions of said control head, including said controls, and said shaft, one of said cover portions comprising combined layers of clear plastic and elastomer providing for the controls to be seen and used through them.

26. A cover system for an endoscope as set forth in claim 25 in which one of said cover portions is latex.

* * * * *